(12) United States Patent
Yanagisawa et al.

(10) Patent No.: US 10,258,047 B2
(45) Date of Patent: Apr. 16, 2019

(54) AGROCHEMICAL COMPOSITE PARTICLES AND PRODUCTION METHOD THEREOF

(71) Applicant: SUMITOMO CHEMICAL COMPANY, LIMITED, Tokyo (JP)

(72) Inventors: Kazuyuki Yanagisawa, Tokyo (JP); Hideo Kawanaka, Takarazuka (JP); Takaaki Yano, Ichihara (JP); Dai Hirotomi, Kasai (JP); Norihisa Sakamoto, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/834,418

(22) Filed: Dec. 7, 2017

(65) Prior Publication Data

US 2018/0160687 A1    Jun. 14, 2018

(30) Foreign Application Priority Data

Dec. 12, 2016 (JP) .................. 2016-240107

(51) Int. Cl.
| | |
|---|---|
| *A01N 59/16* | (2006.01) |
| *A01N 25/26* | (2006.01) |
| *A01N 25/28* | (2006.01) |
| *A01N 43/56* | (2006.01) |
| *A01N 43/84* | (2006.01) |
| *A01N 51/00* | (2006.01) |
| *A01N 63/00* | (2006.01) |

(52) U.S. Cl.
CPC ............. *A01N 59/16* (2013.01); *A01N 25/26* (2013.01); *A01N 25/28* (2013.01); *A01N 43/56* (2013.01); *A01N 43/84* (2013.01); *A01N 51/00* (2013.01); *A01N 63/00* (2013.01)

(58) Field of Classification Search
CPC ........ A01N 25/14; A01N 25/34; A01N 59/16; A01N 63/00; A01N 51/00
See application file for complete search history.

(56) References Cited

U.S. PATENT DOCUMENTS

| | | |
|---|---|---|
| 2006/0246151 A1 | 11/2006 | Anderson |
| 2008/0031832 A1 | 2/2008 | Wakefield et al. |
| 2010/0204283 A1 | 8/2010 | Dairiki et al. |

(Continued)

FOREIGN PATENT DOCUMENTS

| | | | |
|---|---|---|---|
| WO | WO 2009/028454 A1 | 3/2009 | |
| WO | 20151172938 | * 11/2015 | ............ A01N 25/04 |
| WO | WO 2015/172938 A1 | 11/2015 | |

OTHER PUBLICATIONS

Extended European Search Report, dated Jan. 29, 2018, for European Application No. 17203979.4.

(Continued)

*Primary Examiner* — Carlos A Azpuru
(74) *Attorney, Agent, or Firm* — Birch, Stewart, Kolasch & Birch, LLP

(57) ABSTRACT

There is provided an agrochemical formulation with an enhanced efficacy of the agrochemical active ingredient, even when a farmer does not perform a mixing operation. Agrochemical active ingredient particles that are solid at 25° C. and zinc oxide particles are mixed to form a layer comprising the zinc oxide particles on the surface of the agrochemical active ingredient particles.

4 Claims, 2 Drawing Sheets

(56) References Cited

U.S. PATENT DOCUMENTS

2011/0070275 A1\* 3/2011 Hidaka .................. A01N 55/02
 424/401
2011/0111957 A1 5/2011 Ishaque et al.
2017/0251671 A1 9/2017 Yanagisawa et al.

OTHER PUBLICATIONS

Kumar et al., "Glutathione Coated Zinc Oxide Nanoparticles: A Promising Material for Pesticide Detection," Energy and Environment Focus, vol. 2, No. 1, 2013 (Jun. 1, 2013), pp. 1-7 (Total 8 pages), XP055441939.

Prasad et al., "Effect of Nanoscale Zinc Oxide Particles on the Germination, Growth and Yield of Peanut," Journal of Plant Nutrition, vol. 35, No. 6, 2012 (Available online Apr. 3, 2012), pp. 905-927 (Total 24 pages), XP055441943.

Sabir et al., "Zinc Oxide Nanoparticles for Revolutionizing Agriculture: Synthesis and Applications," The Scientific World Journal, Article ID 925494, vol. 2014, Jan. 1, 2014, (Published Nov. 11, 2014), pp. 1-8 (Total 9 pages), XP055441944.

\* cited by examiner

US 10,258,047 B2

AGROCHEMICAL COMPOSITE PARTICLES AND PRODUCTION METHOD THEREOF

BACKGROUND OF THE INVENTION

Field of the Invention

The present invention relates to agrochemical composite particles in which solid agrochemical active ingredient particles are coated with zinc oxide and a production method thereof.

Description of the Related Art

So far, various studies have been conducted for the purpose of enhancing an efficacy of agrochemical active ingredients. For example, a method for enhancing an efficacy of an agrochemical active ingredient, by mixing the agrochemical active ingredients with a compound having a specific polyoxyalkylene structure in the molecule followed by applying it is known (see WO 2009/028454).

SUMMARY OF THE INVENTION

However, in the conventional method for enhancing an efficacy, a farmer needed to mix an agrochemical active ingredient with the compound.

The present inventors found that an efficacy of the agrochemical active ingredient could be enhanced by mixing agrochemical active ingredient particles that are solid at 25° C. and zinc oxide particles to form a layer comprising the zinc oxide particles on the particle surface of the agrochemical active ingredient particles.

The present invention is as described below.
[1] A method for producing agrochemical composite particles, including a step of mixing agrochemical active ingredient particles that are solid at 25° C. and zinc oxide particles to form a layer comprising the zinc oxide particles on the particle surface of the agrochemical active ingredient, wherein the step is performed by a mechanical particle composing method.
[2] The method for producing agrochemical composite particles according to [1], wherein the particle diameter of the agrochemical active ingredient particles is in the range of 1 to 50 μm.
[3] The method for producing agrochemical composite particles according to [1] or [2], wherein the particle diameter of the zinc oxide particles is one fifth or less of the particle diameter of the agrochemical active ingredient particles.
[4] A method for producing an agrochemical formulation, including a step of formulating agrochemical composite particles produced by the method for producing agrochemical composite particles as defined in any one of [1] to [3].
[5] A method for enhancing an efficacy of an agrochemical active ingredient, including a step of mixing agrochemical active ingredient particles that are solid at 25° C. and zinc oxide particles to form a layer comprising the zinc oxide particles on the particle surface of the agrochemical active ingredient.
[6] Agrochemical composite particles comprising zinc oxide and an agrochemical active ingredient that is solid at 25° C., having a layer comprising the zinc oxide particles on the particle surface of the agrochemical active ingredient.

By producing the agrochemical composite particles of the present invention (hereinafter, referred to as the present composite particles) according to the production method of the present invention, an efficacy of a solid agrochemical active ingredient can be enhanced. The present composite particles have almost same particle diameter as the particle diameter of the agrochemical active ingredient before being coated, and can be formulated similarly as an uncoated agrochemical active ingredient. The present composite particles and an agrochemical formulation obtained by formulating the present composite particles can save the labor for farm work since a farmer does not need to mix an efficacy-enhancing component on an application.

DETAILED DESCRIPTION OF THE PREFERRED EMBODIMENTS

Figure 1:
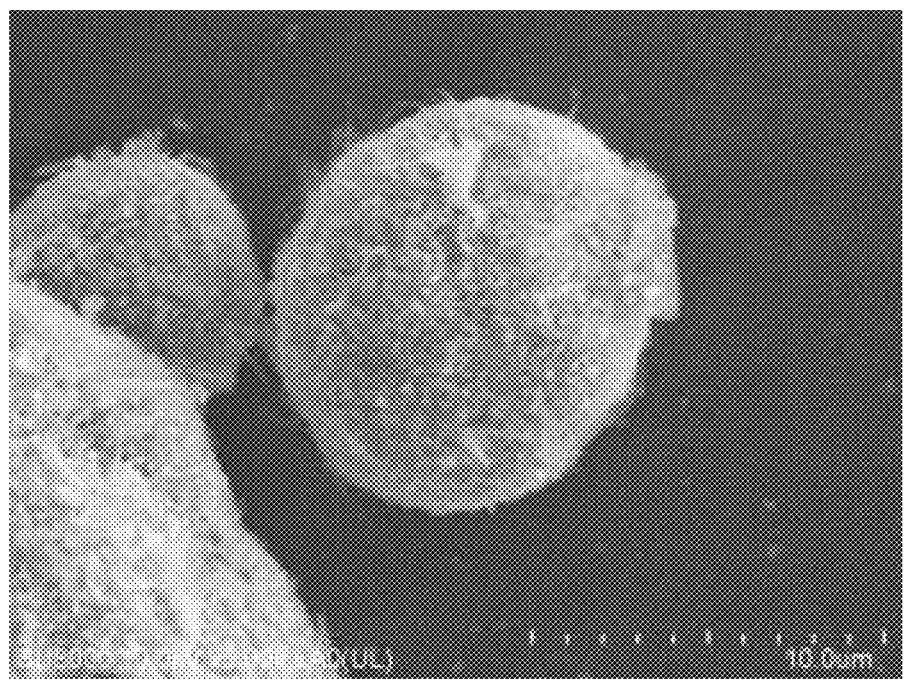
FIG. 1 is an electron micrograph of the present composite particles (Test Example 1)

The agrochemical active ingredient in the present invention is an agrochemical active ingredient that is solid at 25° C., and its melting point is preferably 70° C. or more. Examples of the agrochemical active ingredient include insecticidal active ingredients, insect growth regulating active ingredients, fungicidal active ingredients, herbicidal active ingredients, and plant growth regulating active ingredients.

Examples of the insecticidal active ingredient and insect growth regulating active ingredient include biological agrochemicals utilizing *Bacillus thuringiensis* and the like; pyrethroid compounds such as deltamethrin, tralomethrin, acrinathrin, tetramethrin, and tefluthrin; carbamate compounds such as propoxur, isoprocarb, xylylcarb, metolcarb, thiodicarb, XMC, carbaryl, pyrimicarb, carbofuran, methomyl, fenoxycarb, and fenobucarb; organophosphorus compounds such as acephate, trichlorfon, tetrachlorvinphos, dimethylvinphos, pyridafenthion, azinphos-ethyl, and azinphos-methyl; urea compounds such as diflubenzuron, chlorfluazuron, lufenuron, hexaflumuron, flufenoxuron, flucycloxuron, cyromazine, diafenthiuron, hexythiazox, novaluron, teflubenzuron, triflumuron, 4-chloro-2-(2-chloro-2-methylpropyl)-5-(6-iodo-3-pyridylmethoxy) pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one, and 1-(2,6-difluorobenzoyl)-3-[2-fluoro-4-(1,1,2,2-tetrafluoroethoxy)phenyl]urea; chloronicotyl compounds such as imidacloprid, acetamiprid, clothianidin, nitenpyram, thiamethoxam, dinotefuran, and thiacloprid; spinosyns such as spinosad; diamide compounds such as flubendiamide, chlorantraniliprole, and cyantraniliprole; phenylpyrazole compounds such as fipronil and ethiprole; tetramic acid compounds such as spirotetramat, spiromesifen, and spirodiclofen; other compounds such as cartap, buprofezin, thiocyclam, bensultap, fenazaquin, fenpyroximate, pyridaben, hydramethylnon, chlorfenapyr, fenproxymate, pymetrozine, pyrimidifen, tebufenozide, tebufenpyrad, triazamate, indoxacarb, sulfluramid, milbemectin, avermectin, boric acid and p-dichlorobenzene.

Examples of the fungicidal active ingredient include pyrazolinone compounds such as fenpyrazamine; mandestrobin; benzimidazole compounds such as benomyl, carbendazim, thiabendazole, and thiophanate-methyl; phenyl carbamate compounds such as diethofencarb; dicarboxylmide compounds such asprocymidone, iprodione, and vinclozolin; azole compounds such as diniconazole, probenazole, epoxyconazole, tebuconazole, difenoconazole, cyproconazole, flusilazole, and triadimefon; acylalanine compounds such as metalaxyl; carboxamide compounds such as furametpyr, mepronil, flutolanil, and trifluzamide; organophosphorus compounds such as tolclophos-methyl, fosetyl-aluminum, and pyrazophos; anilinopyrimidine compounds such as pyrimethanil, mepanipyrim, and cyprodinil; cyanopyrrole compounds such as fludioxonil and fenpiclonil; antibiotics such as blastocidin S, kasugamycin, polyoxin, and validamycin; methoxyacrylate compounds such as azoxystrobin, kresoxim-methyl, and SSF-126; other compounds such as chlorothalonil, mancozeb, captan, folpet, tricyclazole, pyroquilon, probenazole, fthalide, cymoxanil, dimethomorph, famoxadone, oxolinic acid, fluazinam, ferimzone, diclocymet, chlobenthiazone, isovaledione, tetrachloroisophthalonitrile, thiophthalimideoxybisphenoxyarsine, 3-iodo-2-propylbutyl carbamate, p-hydroxybenzoate, sodiumdehydroacetate, potassium sorbate, orysastrobin, isotianil, tiadinil, and thiuram.

Examples of the herbicidal active ingredient include triazine compounds such as atrazine and metribuzin; urea compounds such as fluometuron and isoproturon; hydroxybenzonitrile compounds such as bromoxynil and ioxynil; 2,6-dinitroaniline compounds such as pendimethalin and trifluralin; aryloxyalkanoic acid compounds such as 2,4-D, dicamba, fluroxypyr, and mecoprop; sulfonylurea compounds such as bensulfuron-methyl, metsulfuron-methyl, nicosulfuron, primisulfuron-methyl, cyclosulfamuron, imazosulfuron, propyrisulfuron, and sulfosulfuron; imidazolinone compounds such as imazapyr, imazaquin, and imazethapyr; other compounds such as bispyribac-Na salt, bisthiobac-Na salt, acifluorfen-Na salt, sulfentrazone, paraquat, flumetsulam, triflusulfuron-methyl, fenoxaprop-p-ethyl, diflufenican, norflurazone, isoxaflutole, glufosinate-ammonium, glyphosate, bentazon, mefenacet, propanil, flutiamide, flumiclorac-pentyl, flumioxazin, and bromobutide.

Examples of the plant growth regulating active ingredient include maleic hydrazide, clormequat, ethephon, gibberellin, mepiquat chloride, thidiazuron, inabenfide, paclobutrazol, and uniconazole.

As the agrochemical active ingredient in the present invention, fenpyrazamine, flumioxazin, clothianidin and biological agrochemicals utilizing *Bacillus thuringiensis* are preferred.

The particle diameter of the agrochemical active ingredient particles in the present invention is in the range of 1 to 50 μm. The particle diameter of the agrochemical active ingredient particles is determined according to the form of selected formulation (formulation type) when formulating the present composite particles. In the case of a formulation type applied as it is (for example, dust formulation and granules), the particle diameter is usually in the range of 2 to 50 μm, preferably 3 to 50 μm, and further preferably 5 to 30 μm, and in the case of a formulation type applied in admixture with water (for example, suspension concentrate and wettable powder), the particle diameter is usually in the range of 1 to 40 μm, preferably 1 to 30 μm, and further preferably 1 to 25 μm. In the present invention, the particle diameter of the agrochemical active ingredient particles means a particle diameter at which a cumulative frequency in a volume-based frequency distribution is to be 50% (Volume median diameter), and can be obtained by wet measurement using a laser diffraction particle diameter distribution measuring apparatus. More specifically, the agrochemical active ingredient particles are dispersed in water, and the particle diameter is measured using the apparatus. Examples of the laser diffraction particle size distribution measuring apparatus include Mastersizer 2000 manufactured by Malvern Instruments Ltd.

In the present invention, agrochemical active ingredient powder pulverized using a pulverizer, as necessary, is used as agrochemical active ingredient particles. Examples of the pulverizer include a jet mill and a centrifugal pulverizer.

The particle diameter of the zinc oxide particles in the present invention is usually one fifth or less and preferably one tenth or less of the particle diameter of the agrochemical active ingredient particles. In the present invention, commercially available zinc oxide can be used. Examples of the commercially available zinc oxide include zinc oxide fine powder (Zinc Oxide for rubber No. 1, No. 2, No. 3, Fine zinc oxide; FINE X-50; NANOFINE-50) manufactured by Sakai Chemical Industry Co., Ltd.

The particle diameter of the zinc oxide particles means a particle diameter (Volume median diameter) obtained by measuring the particle diameter of zinc oxide particles in a zinc oxide dispersion liquid using dynamic light scattering method. More specifically, the particle diameter is obtained as a particle size distribution by measuring the particle diameter in the zinc oxide dispersion liquid using the ZETASIZER Nano ZSP (manufactured by Malvern Instruments Ltd.) under the following operating conditions: (i) The refractive index of solvent is 1330, (ii) The viscosity of solvent is 0.8872 cp, (iii) The sample temperature is 25° C., (iv) The equilibration time is 20 seconds. The zinc oxide dispersion liquid is prepared by adding zinc oxide fine powder into a glass screw tube containing 100 mL of ion exchanged water so that the content of zinc oxide may be 0.01%, followed by irradiating the glass screw tube with ultrasonic waves for 60 seconds.

The method for producing the present composite particles (hereinafter, referred to as the method for producing the present composite particles) will be described below.

The method for producing the present composite particles includes a step of mixing agrochemical active ingredient particles that are solid at 25° C. and zinc oxide particles to form a layer comprising the zinc oxide particles on the particle surface of the agrochemical active ingredient (hereinafter, referred to as the present step). The present step is performed by a mechanical particle composing method. The mechanical particle composing method is a method for preparing composite particles using machines such as pulverizer and mixer, and is known as a technology for coating particles of a matter to be a nucleus (hereinafter, referred to as mother particles) with many particles that are a matter different from mother particles and smaller than the mother particles (hereinafter, referred to as child particles) to prepare composite particles without using a binder, by adding mechanical energy such as compression, shear, friction and impact to a mixture of the mother particles and the child particles. The technology is described in many documents, and examples of the document include "Next-generation particulate coating technologies for the development of pharmaceutical preparations" (supervised by Hideki Ichikawa, CMC Publishing Co., Ltd., Dec. 3, 2012, p. 111 to 118). The mechanical particle composing method can be performed by using a commercially available particle composing machine. Examples of the commercially available particle composing machine include high-speed impact dry particle composing machines such as Nara Hybridization System (registered trademark) manufactured by Nara Machinery Co., Ltd. and KRYPTRON manufactured by EARTHTECHNICA CO., LTD. and compression and shearing dry particle composing machines such as MECHANO FUSION (registered trademark) manufactured by HOSOKAWA MICRON CORPORATION, NOBILTA (registered trademark) NOB manufactured by HOSOKAWA MICRON CORPORATION that is an apparatus described in JP-A-2005-270955, and Theta Composer manufactured by TOKUJU CORPORATION. The present step is preferably performed using NOBILTA.

In the present step, agrochemical active ingredient powder and zinc oxide powder are used as mother particles and child particles, respectively. When a compound obtained by blending agrochemical active ingredient powder and zinc oxide powder in a predetermined ratio is mixed with a particle composing machine, the zinc oxide particles adhere to the surface of the agrochemical active ingredient particles to form a layer comprising the zinc oxide particles. The weight ratio of the agrochemical active ingredient powder to the zinc oxide powder can be varied depending on particle diameter and true specific gravity of the agrochemical active ingredient particles, and particle diameter and true specific gravity of the zinc oxide, and is in the range of usually 4:96 to 99.7:0.3, preferably 16:84 to 99.4:0.6, and further preferably 25:75 to 99:1. The term 'true specific gravity' here is measured using pycnometer method. In the present step, it is possible to charge the total amount of the agrochemical active ingredient powder and the zinc oxide powder at a time, or it is also possible to charge the whole amount of the agrochemical active ingredient powder and dividedly charge the zinc oxide powder, into a mixing vessel of the particle composing machine. When charging the total amount of the agrochemical active ingredient powder and the zinc oxide powder at a time into a mixing vessel of the particle composing machine, it is possible to separately charge the agrochemical active ingredient powder and the zinc oxide powder into the mixing vessel of the particle composing machine, or it is also possible to charge a mixture obtained by previously mixing the agrochemical active ingredient powder and the zinc oxide powder using a mixer such as a Nauta Mixer (registered trademark) manufactured by HOSOKAWA MICRON CORPORATION. After charging the total amount of the agrochemical active ingredient powder and the zinc oxide powder into a mixing vessel of the particle composing machine, the powder is mixed by operating the particle composing machine, whereby the present composite particles can be obtained.

When charging the whole amount of the agrochemical active ingredient powder and dividedly charging the zinc oxide powder, into a mixing vessel of the particle composing machine, a step of, first, charging the whole amount of the agrochemical active ingredient powder and a part of the zinc oxide powder into a mixing vessel of the particle composing machine and mixing the powder by operating the particle composing machine to obtain composite particles (hereinafter, referred to as step 1) is carried out. Next, a step of adding a part of the zinc oxide powder and mixing the composite particles obtained in the step 1 and the zinc oxide powder by operating the particle composing machine to coat the composite particles with the zinc oxide (hereinafter, referred to as step 2) is repeatedly carried out, whereby the present composite particles can be obtained. Also, after carrying out the step 1, a part of the obtained composite particles is taken out of the machine, and the zinc oxide in the same amount as the taken composite particles can be added in the step 2.

The mixing intensity when mixing with a particle composing machine is in the range of usually 0.001 to 0.25 kW/g, and preferably 0.005 to 0.05 kW/g. In the present invention, the mixing intensity refers to a value obtained by dividing the power (kW) of the particle composing machine at mixing by the charge amount (g) of the powder into the mixing vessel of the particle composing machine. Also, the mixing time is usually in the range of 0.5 to 20 minutes and preferably 3 to 15 minutes.

The value of the specific surface area of the present composite particles is in the range of usually ½ to $\frac{1}{20}$ and preferably ½ to $\frac{1}{10}$ of the value of the specific surface area of the mixture obtained by simply mixing the agrochemical active ingredient powder and the zinc oxide powder. In the present invention, the specific surface area refers to a value obtained by BET method. Specifically, the specific surface area is obtained by analyzing by BET method (analysis method using a formula of BET) an adsorption-desorption isotherm obtained by determining a powder particle surface pretreated by vacuum deaeration at about 25° C. for about 12 hours using BELPREP-VAC II (manufactured by BEL Japan, Inc.) by a constant volume method of nitrogen adsorption method using BELSORP-mini (manufactured by BEL Japan, Inc.).

Figure 2:
FIG. 2 is an electron micrograph of the cross section of the present composite particles (Test Example 2)
Figure 3:
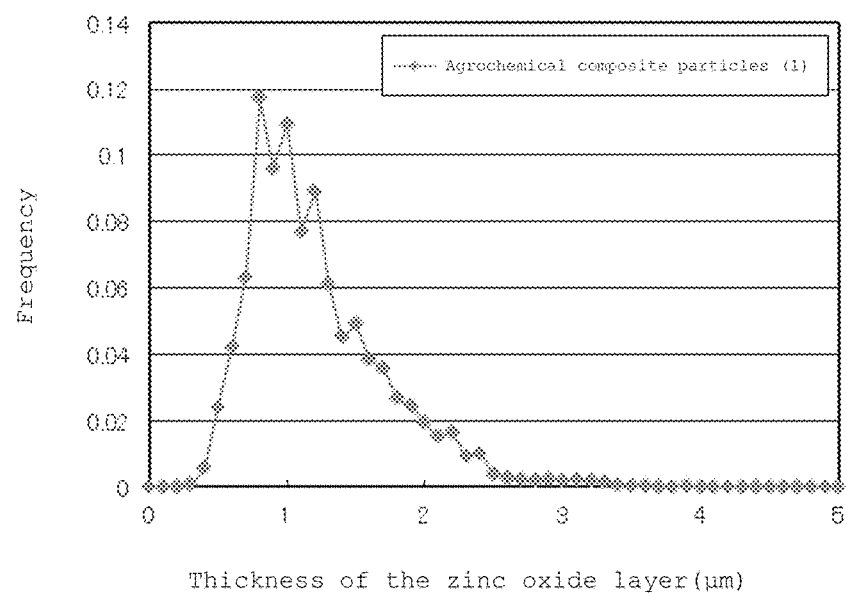
FIG. 3 is a graph showing a thickness distribution of a zinc oxide layer of the present composite particles (Test Example 2).

FIG. 1 and FIG. 2 are electron micrographs of the present composite particles. As shown in FIG. 1, the present composite particles are covered with a layer comprising many zinc oxide particles (hereinafter, referred to as zinc oxide layer) on the surface of one particle of the agrochemical active ingredient. Not all the surface of the agrochemical active ingredient particles may be necessarily covered with zinc oxide. In the present invention, it is preferred that 50% or more of the surface of the agrochemical active ingredient particles is covered with zinc oxide, and further preferred that 100% of the surface of the agrochemical active ingredient particle is covered with zinc oxide. FIG. 2 shows the cross section of the present composite particles. Almost all the surface of the agrochemical active ingredient particle is covered with many zinc oxide particles, and the zinc oxide particles form a layer and cover the surface of the agrochemical active ingredient.

Generally, it is preferred that 100% of the surface of the agrochemical active ingredient particles is covered, and also the zinc oxide layer has a uniform thickness. The average thickness of the zinc oxide layer is in the range of usually 0.01 to 100 μm, preferably 0.05 to 50 μm, and more preferably 0.1 to 20 μm.

The average thickness of the zinc oxide layer is obtained as below. The present composite particles are embedded in a resin, and the cross section is prepared using a microtome. In a digital image of the cross section observed with a scanning electron microscope, the agrochemical active ingredient particles, the zinc oxide layer and the embedded resin part outside of the present composite particles are ternarized to gray, white, and black, respectively. Thereafter, using pixels at the boundary between the white part and the gray part as a starting point, the shortest distance from the starting point to the boundary between the white part and the black part is obtained by image analysis, and this operation is performed at all starting points. The number average of thousands to several tens of thousands of distances obtained by performing the similar image analysis for several tens to about a hundred of the present composite particles is an average thickness of the zinc oxide layer.

Also, the particle diameter of the present composite particles is 1.0 to 1.5 times the particle diameter of the agrochemical active ingredient particles. The present composite particles preferably have a wet sieve residue of 2% or less. In the present invention, the wet sieve residue is a value obtained by the following method. First, a formulation containing the present composite particles is diluted 100 times with ion-exchanged water, and stirred with a magnetic stirrer or the like, and the obtained dispersion liquid is passed through a sieve having 300 µm openings, and washed with tap water until the amount of residue becomes constant. Subsequently, the residue on the sieve is transferred to a petri dish, and water is evaporated, then the weight of the residue is measured. The ratio (%) of the residue weight based on the composite particles used in the test is the wet sieve residue.

The content of zinc oxide in the present composite particles is usually 0.3 to 96% by weight, preferably 0.6 to 84% by weight, and further preferably 1 to 75% by weight. Also, the weight ratio of the agrochemical active ingredient to the zinc oxide in the present composite particles can be varied depending on the particle diameter and true specific gravity of the agrochemical active ingredient particles, and the particle diameter and true specific gravity of the zinc oxide, and is in the range of usually 4:96 to 99.7:0.3, preferably 16:84 to 99.4:0.6, and further preferably 25:75 to 99:1.

The method for producing an agrochemical formulation of the present invention includes a step of formulating the present composite particles. The present composite particles can be formulated similarly as a solid agrochemical active ingredient that is not composed. Also, the present composite particles are adjusted to a desired particle size at making a composite, thus do not need to be pulverized at formulation. Formulation is performed by a known method. When the present composite particles and a formulation auxiliary such as solid inert carriers, binders and surfactants are mixed, it can be formulated into a solid formulation such as wettable powder, dust formulation, DL (driftless) dust formulation, granules, micro granules, micro granules F, water dispersible granules, jumbo formulation, and tablet. Also, when the present composite particles, a dispersion medium such as water and organic solvents, and a formulation auxiliary such as surfactants are mixed, it can be formulated into a liquid formulation such as suspension concentrate, aqueous emulsion formulation and oil flowable.

The agrochemical formulation obtained by formulating the present composite particles can be used in the same manner as a conventional agrochemical formulation, and can be applied to places such as paddy fields, cultivated lands, orchards, grass plot, and non-agricultural lands. The formulation may be mixed with water as desired, and sprayed on plants growing in the above places or the soil in the above places. The method for spraying a pesticide liquid obtained by mixing the formulation with water includes a soil surface application or foliage application using a known sprinkler or the like, and the like. It is also possible to use the pesticide liquid in a seed treatment, a seedling raising box treatment, and the like.

The method for enhancing an efficacy of the present invention includes a step of mixing agrochemical active ingredient particles that are solid at 25° C. and zinc oxide particles to form a layer comprising the zinc oxide particles on the particle surface of the agrochemical active ingredient. According to the method for enhancing an efficacy of the agrochemical active ingredient of the present invention, the efficacy of the solid agrochemical active ingredient which is used can be enhanced.

The present composite particles comprise zinc oxide and an agrochemical active ingredient that is solid at 25° C., having a layer comprising the zinc oxide particles on the particle surface of the agrochemical active ingredient. The present composite particles have almost same particle diameter as the particle diameter of the agrochemical active ingredient before being coated, and therefore they can be formulated similarly as an uncoated agrochemical active ingredient which is solid at 25° C.

EXAMPLES

Next, the present invention will be further described in detail by examples, and the like. However, the present invention is not limited only to these examples.

Reference Production Example 1

Fenpyrazamine (Purity: 98.4%, manufactured by Sumitomo Chemical Co., Ltd.) was dry-pulverized using a vertical jet mill (JOM-0101 model jet crusher, manufactured by Seishin Enterprise Co., Ltd.) with changing air pressure to obtain fenpyrazamine powder having a particle diameter of 5.0 µm (hereinafter, referred to as fenpyrazamine powder A) and fenpyrazamine powder having a particle diameter of 6.0 µm (hereinafter, referred to as fenpyrazamine powder B).

Production Example 1

Nine point six grams (9.6 g) of fenpyrazamine powder B and 2.4 g of zinc oxide powder (Fine Zinc Oxide for rubber, manufactured by Sakai Chemical Industry Co., Ltd.) were charged into a mixing vessel of a particle composing machine (NOBILTA NOB-MINI, manufactured by HOSOKAWA MICRON CORPORATION), and mixed at a power of 87 to 187 W for 10 minutes to obtain composite particles 1a. Two grams (2.0 g) of the composite particles 1a was taken out from the mixing vessel, and 2.0 g of zinc oxide powder (the same as described above) was added thereto, then the mixture was mixed at a power of 55 to 60 W for 10 minutes to obtain agrochemical composite particles (1) of the present invention (hereinafter, referred to as agrochemical composite particles (1)).

The content of fenpyrazamine in the agrochemical composite particles (1) was 54.9% (w/w). The particle size of the zinc oxide powder was measured using above mentioned ZETASIZER Nano ZSP, and it was found that the particle diameter of the zinc oxide powder was 460 nm.

Production Example 2

Nine point six grams (9.6 g) of fenpyrazamine powder A and 2.4 g of zinc oxide powder (the same as described above) were charged into a mixing vessel of a particle composing machine (the same as described above), and mixed at a power of 78 to 257 W for 10 minutes to obtain composite particles 2a. Two grams (2.0 g) of the composite particles 2a was taken out from the mixing vessel, and 2.0 g of zinc oxide powder (the same as described above) was added thereto, then the mixture was mixed at a power of 70 to 78 W for 10 minutes to obtain agrochemical composite particles (2) of the present invention (hereinafter, referred to as agrochemical composite particles (2)).

Production Example 3

Clothianidin was dry-pulverized using a vertical jet mill (the same as described above) to obtain clothianidin powder having a particle diameter of 3.5 μm. Nine point six grams (9.6 g) of the clothianidin powder and 2.4 g of zinc oxide powder (the same as described above) were charged into a mixing vessel of a particle composing machine (the same as described above), and mixed at a power of 257 to 284 W for 10 minutes to obtain composite particles 3a. Two grams (2.0 g) of the composite particles 3a was taken out from the mixing vessel, and 2.0 g of zinc oxide powder (the same as described above) was added thereto, then the mixture was mixed at a power of 214 to 239 W for 10 minutes to obtain agrochemical composite particles (3) of the present invention (hereinafter, referred to as agrochemical composite particles (3)).

Production Example 4

Viable *Bacillus thuringiensis* kurstaki (hereinafter, referred to as BT) was dry-pulverized using a vertical jet mill (the same as described above) to obtain BT powder having a particle diameter of 21 μm. Nine point six grams (9.6 g) of the BT powder and 2.4 g of zinc oxide powder (the same as described above) were charged into a mixing vessel of a particle composing machine (the same as described above), and mixed at a power of 148 to 158 W for 10 minutes to obtain agrochemical composite particles (4) of the present invention (hereinafter, referred to as agrochemical composite particles (4)).

Formulation Example 1

Point four (0.4) parts by weight of magnesium aluminum silicate (trade name: VEEGUM (registered trademark) R, manufactured by Vanderbilt Minerals, LLC) was added to 14.2 parts by weight of deionized water, and the mixture was stirred at room temperature for 15 minutes. Point two (0.2) parts by weight of xanthan gum (trade name: KELZAN (registered trademark) S, manufactured by CP Kelco) and 5 parts by weight of propylene glycol were added thereto, andmixed therewith to obtain a mixture. The mixture was stirred at 60° C. for 60 minutes, and the obtained dispersion liquid was cooled to room temperature, then 0.2 parts by weight of a preservative (trade name: Proxel GXL, manufactured by Lonza) was added to the dispersion liquid to obtain a viscosity adjusting liquid. Twenty (20) parts by weight of the viscosity adjusting liquid, 18.2 parts by weight of the agrochemical composite particles (1), 5 parts by weight of sodium lignin sulfonate (trade name: REAX (registered trademark) 85A, manufactured by MeadWestvaco Corporation) and 56.8 parts by weight of deionized water were mixed to obtain a suspension concentrate (1).

Formulation Example 2

Thirty five (35) parts by weight of the agrochemical composite particles (2), 5 parts by weight of sodium alkylnaphthalene sulphonate (Morwet (registered trademark) EFW, manufactured by Akzo Nobel N.V.), 15 parts by weight of a formalin condensate of sodium naphthalene sulfonate (Morwet (registered trademark) D-425, manufactured by Akzo Nobel N.V.) and 45 parts by weight of agalmatolite (trade name: Shokozan clay S, manufactured by SHOKOZAN MINING Co., Ltd.) were mixed using a mortar to obtain wettable powder (1).

Formulation Example 3

Thirty (30) parts by weight of the agrochemical composite particles (3), 5 parts by weight of sodium alkylnaphthalene sulphonate (the same as described above), 15 parts by weight of a formalin condensate of sodium naphthalene sulfonate (the same as described above) and 50 parts by weight of agalmatolite (the same as described above) were mixed using a mortar to obtain wettable powder (2).

Formulation Example 4

One point two five (1.25) parts by weight of the agrochemical composite particles (4), 0.13 parts by weight of liquid paraffin (trade name: Driless C, manufactured by DAIICHI SANKYO COMPANY, LIMITED), 0.07 parts by weight of wet-process silica (trade name: Tokusil NP, manufactured by Tokuyama Siam Silica Co., Ltd.) and 98.55 parts by weight of dry clay (trade name: DL clay, manufactured by HAYASHI KASEI CO., LTD.) were mixed using a juice blender to obtain a dust formulation (1).

Reference Production Example 2

Fifty six (56) parts by weight of fenpyrazamine powder B and 44 parts by weight of zinc oxide powder (the same as described above) were put in a polyethylene bag, and the polyethylene bag was vigorously shaken to mix the powders to obtain a mixture (1) of fenpyrazamine and zinc oxide for comparison (hereinafter, referred to as a comparative mixture (1)).

Reference Formulation Example 1

Twenty one (21) parts by weight of fenpyrazamine powder A, 5 parts by weight of sodium alkylnaphthalene sulphonate (the same as described above), 15 parts by weight of a formalin condensate of sodium naphthalene sulfonate (the same as described above) and 59 parts by weight of agalmatolite (the same as described above) were mixed using a juice blender to obtain wettable powder (1) for comparison (hereinafter, referred to as comparative wettable powder (1)).

Reference Formulation Example 2

Twenty (20) parts by weight of fenpyrazamine powder A, 16 parts by weight of zinc oxide powder (the same as described above), 5 parts by weight of sodium alkylnaphthalene sulphonate (the same as described above), 15 parts by weight of a formalin condensate of sodium naphthalene sulfonate (the same as described above) and 44 parts by weight of agalmatolite (the same as described above) were mixed using a juice blender to obtain wettable powder (2) for comparison (hereinafter, referred to as comparative wettable powder (2)).

Reference Formulation Example 3

Twenty (20) parts by weight of the clothianidin powder obtained in Production Example 3, 10 parts by weight of zinc oxide powder (the same as described above), 5 parts by weight of sodium alkylnaphthalene sulphonate (the same as described above), 15 parts by weight of a formalin condensate of sodium naphthalene sulfonate (the same as described above) and 50 parts by weight of agalmatolite (the same as described above) were mixed using a juice blender to obtain wettable powder (3) for comparison (hereinafter, referred to as comparative wettable powder (3)).

Reference Formulation Example 4

One (1) part by weight of the BT powder obtained in Production Example 4, 4 parts by weight of zinc oxide powder (the same as described above), 0.13 parts by weight of liquid paraffin (the same as described above), 0.07 parts by weight of wet-process silica (the same as described above) and 94.8 parts by weight of dry clay (the same as described above) were mixed using a juice blender to obtain a dust formulation (1) for comparison (hereinafter, referred to as a comparative dust formulation (1)).

Test Example 1

The agrochemical composite particles (1) were observed using a scanning electron microscope (model type: S-5500, manufactured by Hitachi, Ltd.). An electron micrograph of the agrochemical composite particles (1) is shown in FIG. 1.

Test Example 2

The agrochemical composite particles (1) were embedded in an epoxy resin, and a particle cross section was prepared using a ultramicrotome (model type: Leica EM UC7, manufactured by Leica Microsystems) and a diamond knife. The particle cross section was observed using a scanning electron microscope (the same as described above). An electron micrograph of the cross section of the agrochemical composite particles (1) is shown in FIG. 2. Also, in a digital image of the observed cross section, as to 25 particles for the agrochemical composite particles (1), the agrochemical active ingredient particles, the zinc oxide layer and the embedded resin part outside of the present composite particles were ternarized to gray, white, and black, respectively. Thereafter, using pixels at the boundary between the white part and the gray part of each particle as a starting point, the shortest distance from the starting point to the boundary between the white part and the black part was obtained by image analysis, and this operation was performed at all starting points. Thickness distribution of zinc oxide layer of the agrochemical composite particles (1) measured by obtaining number average of distance at 22189 points (the agrochemical composite particles (1)) obtained by performing the similar image analysis for all particles is shown in FIG. 3.

Test Example 3

The agrochemical composite particles (1) and the comparative mixtures (1) were each pretreated by vacuum deaeration at about 25° C. for about 12 hours using BEL-PREP-VAC II (manufactured by BEL Japan, Inc.), then the specific surface area was calculated by BET method from an adsorption-desorption isotherm measured by a constant volume method of nitrogen adsorption method using BEL-SORP-mini (manufactured by BEL Japan, Inc.). The result is shown in Table 1.

TABLE 1

| | Specific surface area ($m^2/g$) |
|---|---|
| Agrochemical composite particles (1) | 1.12 |
| Comparative mixture (1) | 5.26 |

Test Example 4

The wettable powder (1) and the comparative wettable powders (1) and (2) were each mixed with water so as to have a concentration of the active ingredient of 50 ppm to each obtain a pesticide liquid. Fifty milliliters (50 mL) of the pesticide liquid was sprayed on the leaf surface of cucumber with a spray gun. After managed in a greenhouse for a week from the day after spraying, a potato decoction agar medium containing genera sclerotinia was inoculated on the leaf surface. This is defined as a treated section.

Also, the same procedure as the treated section was carried out except that spraying of the pesticide liquid was not conducted. This is defined as a non-treated section.

Thereafter, the cucumber was placed under high humidity for 3 days, then the diameter of lesions formed on the leaf surface of the cucumber was measured. As a result, while lesions with 32% and 61% of the diameter of that in the non-treated section were each found on the leaf surface on which the comparative wettable powders (1) and (2) were each sprayed, lesion with 8% of the diameter of that in the non-treated section was found on the leaf surface on which the wettable powder (1) was sprayed.

Test Example 5

The wettable powder (2) and the comparative wettable powder (3) were each mixed with a spreading agent (trade name: Shindain) solution diluted 5000 times (using ion-exchanged water) so as to have a concentration of the active ingredient of 1000 ppm to each obtain a pesticide liquid. Twenty five milliliters (25 mL) of the pesticide liquid was sprayed on 6 heads of potted cabbage with a spray gun. After spray treatment, the cabbage was managed in a glass house. This is defined as a treated section.

Also, the same procedure as the treated section was carried out except that spraying of the pesticide liquid was not conducted. This is defined as a non-treated section.

After 7 weeks, the number of *Thrips tabaci* Lindeman parasitic on the cabbage was all counted. As a result, while 50 parasites in the non-treated section and 37 parasites in the treated section on which the comparative wettable powder (3) was sprayed were found, 7 parasites were found in the treated section on which the wettable powder (2) was sprayed.

Test Example 6

Each 3120 mg of the dust formulation (1) and the comparative dust formulation (1) was sprayed on 6 heads of potted cabbage with a small manual dust formulation sprinkler. After spray treatment, the cabbage was managed in a glass house. This is defined as a treated section.

Also, the same procedure as the treated section was carried out except that spraying of the pesticide was not conducted. This is defined as a non-treated section.

After a week, one leaf was cut off from each head and placed in a 500-ml plastic cup with 10 second-instar larvae of *Plutella xylostella*, and after 7 days, the insect mortality (including toxication) rate was investigated. As a result, while the insect mortality (including toxication) rate was 16.7% in the non-treated section and 50% in the treated section on which the comparative dust formulation (1) was sprayed, the insect mortality rate was 80% in the treated section on which the dust formulation (1) was sprayed.

The present composite particles can be easily formulated. An agrochemical formulation obtained by formulating the present composite particles can improve an efficacy of the agrochemical active ingredient, even when a farmer does not mix an efficacy-enhancing component on an application.

What is claimed is:

1. A method for producing agrochemical composite particles, comprising a step of mixing agrochemical active ingredient particles that are solid at 25° C. and zinc oxide particles to form a layer comprising the zinc oxide particles on the particle surface of the agrochemical active ingredient, wherein the step is performed by a mechanical particle composing method, wherein the particle diameter of the agrochemical active ingredient particles is in the range of 1 to 50 µm.

2. The method for producing agrochemical composite particles according to claim 1, wherein the particle diameter of the zinc oxide particles is one fifth or less of the particle diameter of the agrochemical active ingredient particles.

3. A method for producing an agrochemical formulation, comprising a step of formulating agrochemical composite particles produced by the method for producing agrochemical composite particles comprising a step of mixing agrochemical active ingredient particles that are solid at 25° C. and zinc oxide particles to form a layer comprising the zinc oxide particles on the particle surface of the agrochemical active ingredient, wherein the step is performed by a mechanical particle composing method.

4. Agrochemical composite particles comprising zinc oxide and an agrochemical active ingredient that is solid at 25° C., having a layer comprising the zinc oxide particles on the particle surface of the agrochemical active ingredient, and wherein the agrochemical composite particles are produced by the method for producing agrochemical composite particles according to claim 1.

* * * * *